US00PP13553P2

(12) United States Plant Patent
Dümmen

(10) Patent No.: US PP13,553 P2
(45) Date of Patent: Feb. 11, 2003

(54) PETUNIA PLANT NAMED 'DUESURLAV'

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 09/996,387

(22) Filed: Nov. 30, 2001

(51) Int. Cl.[7] ..... A01H 5/00
(52) U.S. Cl. ..... Plt./356
(58) Field of Search ..... Plt./356

(56) References Cited

U.S. PATENT DOCUMENTS

PP6,915 P * 7/1989 Tsuda et al. ..... Plt./356
PP9,556 P * 5/1996 Tachibana et al. ..... Plt./356
PP10,427 P * 6/1998 Danziger ..... Plt./356

OTHER PUBLICATIONS

UPOV–ROM GTITM Computer Database, 2002/03, GTI Retrieval Software, citation for 'Duesurlav'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Petunia plant named 'Duesurlav', characterized by its upright and outwardly spreading plant habit; freely basal branching; single flowers that are lavender purple in color.

1 Drawing Sheet

BOTANICAL CLASSIFICATION/CULTIVAR DESIGNATION

*Petunia×hybrida* cultivar Duesurlav.

BACKGROUND OF THE INVENTION

The present Invention relates to a new and distinct cultivar of Petunia plant, botanically known as *Petunia×hybrida,* and hereinafter referred to by the cultivar name Duesurlav.

The new Petunia is a product of a planned breeding program conducted by the Inventor in Rheinberg, Germany. The objective of the breeding program is to create new Petunias with attractive flower colors.

The new Petunia originated from a cross made by the Inventor of a proprietary Petunia selection identified as code number 94-206, not patented, as the female, or seed parent, with a proprietary Petunia selection identified as code number D-18-7-02, not patented, as the male, or pollen parent. The new Petunia was selected as a single plant from the resulting progeny by the Inventor in Rheinberg, Germany, on the basis of its attractive flower color.

Asexual reproduction of the new cultivar by terminal vegetative cuttings taken in Rheinberg, Germany has shown that the unique features of this new Petunia are stable and reproduced true to type in successive generations.

SUMMARY OF THE INVENTION

Plants of the cultivar Duesurlav have not been observed under all possible environmental conditions. The phenotype may vary somewhat with variations in environment such as temperature and light intensity without, however, any variance in genotype.

The following traits have been repeatedly observed and are determined to be the unique characteristics of 'Duesurlav'. These characteristics in combination distinguish 'Duesurlav' as a new and distinct cultivar:

1. Upright and outwardly spreading plant habit.
2. Freely basal branching.
3. Single flowers that are lavender purple in color.

Plants of the new Petunia differ primarily from plants of the female parent, the selection 94-206, in flower color as plants of the female selection have white-colored petals. Compared to plants of the male parent, the selection D-18-7-02, plants of the new Petunia have smaller leaves and differ in flower color as plants of the male parent have red-colored petals.

Plants of the new Petunia are similar to plants of the cultivar Fortunia Lavender, not patented, in flower color. However, in side-by-side comparisons conducted in Rheinberg, Germany, plants of the new Petunia differed from plants of the cultivar Fortunia Lavender in the following characteristics:

1. Plants of the new Petunia had larger leaves with longer petioles than plants of the cultivar Fortunia Lavender.
2. Plants of the new Petunia had larger flowers than plants of the cultivar Fortunia Lavender.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Petunia.

The photograph comprises a top perspective view of typical flowers, leaves and stems of 'Duesurlav'.

DETAILED BOTANICAL DESCRIPTION

The cultivar Duesurlav has not been observed under all possible environmental conditions. The phenotype may vary somewhat with variations in environment such as temperature, light intensity and daylength without, however, any variance in genotype.

The aforementioned photographs, following observations and measurements describe plants grown in Rheinberg, Germany, under commercial practice in a glass-covered greenhouse. Plants were about 16 weeks from cuttings and were grown in containers. During the production of the plants, day and night temperatures averaged 18° C. and light levels were about 4,500 lux.

In the following description, color references are made to The Royal Horticultural Society Colour Chart, edition 1995, except where general terms of ordinary dictionary significance are used.

Botanical classification: *Petunia×hybrida* cultivar Duesurlav.

Parentage:

*Female parent*.—Proprietary *Petunia×hybrida* selection identified as code number 94-206, not patented.

*Male parent*.—Proprietary *Petunia×hybrida* selection identified as code number D-18-7-02, not patented.

Propagation:

*Type cutting*.—Terminal vegetative cuttings.

*Time to initiate roots*.—Summer: About 7 days at 20° C. Winter: About 10 days at 20° C.

*Time to develop roots*.—Summer: About 21 days at 20° C. Winter: About 28 days at 20° C.

*Root description*.—Fine, fibrous, white in color.

*Rooting habit*.—Freely branching.

Plant description:

*Form*.—Annual flowering plant; indeterminate; upright and outwardly spreading; eventually cascading. Freely basal branching with about seven lateral branches per plant.

*Usage*.—Appropriate for hanging baskets, window boxes, patio containers and landscape applications.

*Plant height*.—About 25 cm.

*Plant diameter*.—About 25 cm.

*Lateral branches*.—Length: About 23 cm. Diameter: About 3 mm. Internode length: About 2.4 cm. Texture: Pubescent. Color: 144B.

*Foliage description*.—Arrangement: Before flowering, alternate, after flowering, opposite; simple. Quantity per lateral branch: About 10. Length: About 6.1 cm. Width: About 2.6 cm. Shape: Ovate to elliptic. Apex: Broadly acute to obtuse. Base: Attenuate. Margin: Entire. Texture: Pubescent; leathery. Venation pattern: Pinnate. Color: Young and fully expanded foliage, upper surface: 137A. Young and fully expanded foliage, lower surface: 137C. Venation, upper and lower surfaces: 144B. Petiole length: About 1.2 cm. Petiole diameter: About 2.5 mm. Petiole color: 144B.

Flower description:

*Flower type and habit*.—Single salverform flowers; flowers face mostly upward or outward; axillary; about three flowers and flower buds per lateral branch.

*Natural flowering season*.—Long day responsive; spring until frost in the autumn; flowering continuous. Plants start flowering about nine weeks after planting.

*Flower longevity on the plant*.—About 4 days; flowers persistent.

*Fragrance*.—None detected.

*Flower size*.—Diameter: About 5.5 cm. Tube length: About 2.7 cm. Throat diameter, distal end: About 1 cm. Tube diameter, proximal end: About 2.5 mm.

*Flower buds*.—Length: About 3.5 cm. Diameter: About 5 mm. Shape: Elongated oblong. Color: 144B.

*Corolla*.—Quantity/arrangement: Five fused petals; funnelform. Petal length from throat: About 2.5 cm. Petal width: About 2.3 cm. Petal shape: Roughly spatulate. Petal apex: Rounded; slightly ruffled. Petal margin: Entire; slightly ruffled. Petal texture: Smooth, velvety. Petal color: Upper surface, when opening and fully opened: 78B to lighter than 78B towards the throat; color does not fade with subsequent development. Lower surface, when opening and fully opened: 76A. Flower throat (inside): Distally, 59A; proximally, 144B. Flower tube (outside): 144B. Venation, upper surface: 78B. Venation, lower surface: 144B. Venation, throat: 59A. Venation, tube: 144B.

*Sepals*.—Arrangement/appearance: Single whorl of five sepals fused at base, star-shaped. Length: About 1 cm. Width: About 2.25 mm. Shape: Strap-like; elongate. Apex: Rounded. Margin: Entire. Texture, both surfaces: Pubescent. Color: Upper surface: 137A. Lower surface: 137C.

*Peduncles*.—Length: About 2 cm. Width: About 1.25 mm. Angle: Erect to slightly bent. Strength: Moderately strong. Texture: Pubescent. Color: 144B.

*Reproductive organs*.—Stamens: Quantity per flower: About five. Anther shape: Ovoid. Anther length: About 3 mm. Anther color: 92B. Pollen amount: Abundant. Pollen color: 122B. Pistils: Quantity per flower: One. Pistil length: About 2.2 cm. Style length: About 1.8 cm. Style color: 144C. Stigma shape: Rounded. Stigma color: 139A. Ovary color: 144B.

*Seed/fruit*.—Seed nor fruit production has not been observed to date.

Disease/pest resistance: Plants of the new Petunia have not been noted to be resistant to pathogens or pests common to Petunia.

It is claimed:

1. A new and distinct cultivar of Petunia plant named 'Duesurlav', as illustrated and described.

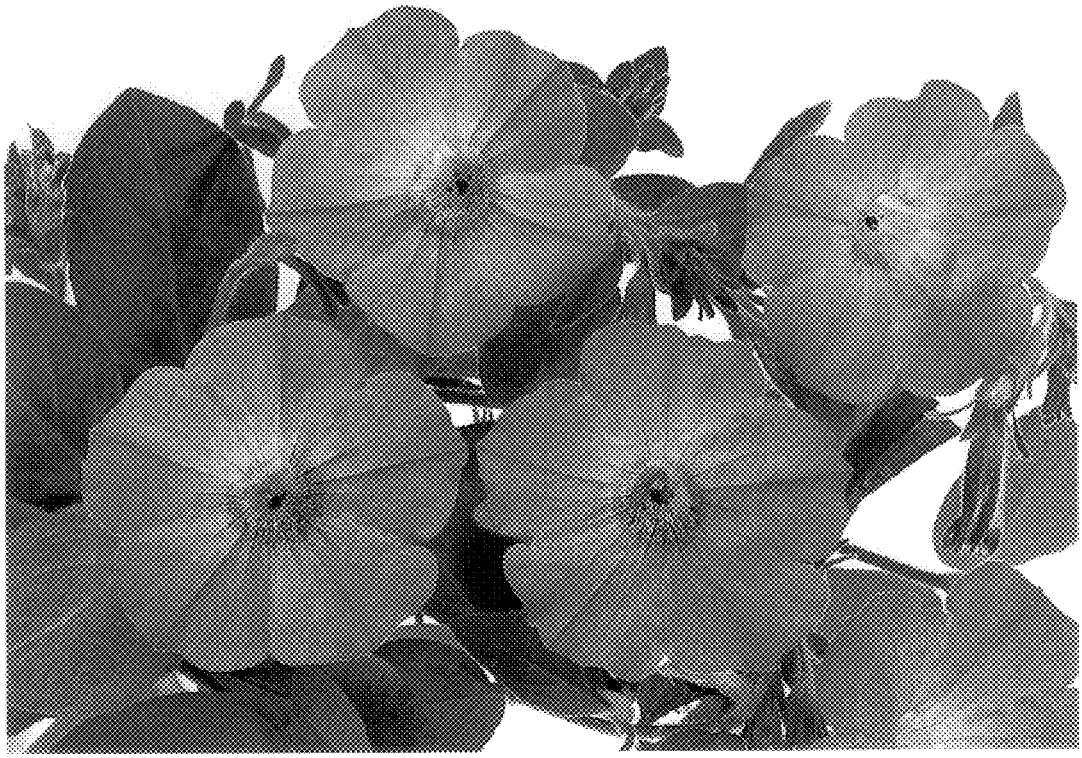

* * * * *